United States Patent [19]
Wu et al.

[11] Patent Number: 6,072,103
[45] Date of Patent: Jun. 6, 2000

[54] PATHOGEN AND STRESS-RESPONSIVE PROMOTER FOR GENE EXPRESSION

[75] Inventors: Gusui Wu, Davis; Thomas E. Holsten, Woodland, both of Calif.

[73] Assignee: Calgene LLC, Davis, Calif.

[21] Appl. No.: 08/976,122

[22] Filed: Nov. 21, 1997

[51] Int. Cl.$^7$ .............................. C12N 5/04; C12N 15/29; C12N 15/82; A01H 5/00
[52] U.S. Cl. ..................... 800/279; 435/69.1; 435/320.1; 435/418; 435/419; 435/468; 536/23.6; 536/24.1; 800/287; 800/301
[58] Field of Search ................................. 435/69.1, 320.1, 435/418, 419, 468; 636/236, 24.1, 24.5; 800/278, 279, 295, 298, 301, 286, 287

[56] References Cited

U.S. PATENT DOCUMENTS 5,689,047  11/1997  Hain et al. ................................. 800/278

FOREIGN PATENT DOCUMENTS 0 464 461  1/1992  European Pat. Off. .
WO 89/12059  12/1989  WIPO ............................ C07H 15/12
WO 97 03205  1/1997  WIPO .

OTHER PUBLICATIONS

Stark–Lorenzen et al, Plant Cell Rep., vol. 16, pp. 668–673, 1997.
Hain et al, Nature, vol. 361, pp. 153–156, 1993.
Broglie et al, Science, vol. 254, pp. 1194–1197, 1991.
Heitz et al, Mol. Gen. Genet., vol. 245, pp. 246–254, 1994.
Hain, R. et al., "Disease Resistance Results from Foreign Phytoalexin Expression in a Novel Plant" *Nature*, vol. 361, Jan. 1993, pp:153–156.

Stark Lorenzen P., et al., "Transfer of a Grapevine Stilbene Synthase Gene to Rice (*Oryza sativa* L.)" *Plant Cell Reports*, vol. 19, Jul. 1997, pp: 668–673.

Schubert, R., et al., "An ozone–responsive region of the grapevine resveratrol synthase promoter differs from the basal pathogen— responsive sequence" Plant Molecular Biology 34:417–426 (1997).

Melchior, F., et al., "Coordinate– and elicitor– Dependent Expression of Stilbene synthase and Phenylalaine Ammonia–Lyase Genes in Vitis cv. Optima" Archives of Biochemistry and Biophysics vol. 288:2 pp. 552–557 (1991).

Wiese, W., et al., "Structural organization and differential expression of three stilbene synthase genes located on a 13 kb grapevine DNA fragment" Plant Molecular Biology 26:667–677, (1994).

*Primary Examiner*—David T. Fox
*Assistant Examiner*—Ashwin D. Mehta

[57] ABSTRACT

Nucleic acid sequences and methods for their use are provided for obtaining plants with inducible phenotypes, including novel or enhanced resistance to infection and stress. Novel nucleic acid constructs are provided, which include a transcriptional initiation region from a pathogen inducible-rapid response grape stilbene synthase gene, a DNA sequence of interest and a transcriptional termination region. The constructs are used to prepare expression cassettes which may then be introduced into plants and portions thereof for modulation of expression of endogenous products as well as production of exogenous products in the plant.

20 Claims, 3 Drawing Sheets

```
                                                              60
ACTATAGGGCACGCGTGGTCGACGGCCCTGGCAAATATATTGGCAAGTGATGCAGGCGAC
                                                             120
AGGTAAATATTTTTTTTACAGACTTCTCTTTCAATAATTCTGTTGTTTATTAAAACAAAT
                                                             180
GTGGCATTTATATTAAACTGCTTTAATATATTTAAGAATGTTATAAAGTATTGTTAAAAT
                                                             240
GCTCTTATAGTCAACATCCACTGTCGTGGGTCCTATGATATGCACATATGATAAATATAC
                                                             300
ACGTATAATGCTATTATATGATGCACACGTTATTACACGATATTTAATTTGTGACTTTCT
                                                             360
TATGGGTACAAATTAAAATTTGTACCAATTTTTGACTTGGCAACCAAAGTCATTGATATT
                                                             420
TTCCAAGTTAAAATTTGTACCAATTAAAATTTGTACAATTTTCCAATGAGTTTGCAAAAT
                                                             480
TCTAATGCTATGAAGATATTTTCAAATCAAATTTATGTGAACAAAAATTAAAGTAGTAGT
                                                             540
TATTTTCCAAGTTATTTCGTGGATATTTGATGGAGACTTGTATTTTTGATCTACTTATTT
                                                             600
ATTTATTTATTTTTAAGAATCAAACGAATGCGCCCCAGCGTCTTGTATCGCGGAATAGGT
                                                             660
CAGATACAAATGAGATATTTGTTCAATTACTATGTGAATAGGTTAAATGACATGTGACGT
                                                             720
TATCCTGGAGAAGAAAGATAGTGGGTTGTTGAGATTATTACTTCTAATTGAGAAATCCAT
                                                             780
CTTTGAATGACCTTGTCATGAGGAATGATGGTAGCAGCTTCCCAGCCGTGGAAAAGTCAA
                                                             840
ATGAACAAAGTATTAATTTCCAGTAAGAGGTTGGAGAAGTCTTTGTCTCTCTATATAAAA
                                                             900
AATGTTTCTCTTTAGCCGTGACCGGATTGAATGCTCGCTCCTTTCTGTGGATGCACGCAT
                                                             960
CGTATATGGGTAGGTGAAGAACAGATAAGAATGAAGAGACAACACGCGCGAATACATAAA
                                                            1020
CACCTACACATACATGTCTGAAAATCCAAAATAAACTCAAGCACACAAGCTTTGAAGCCA
```

FIGURE 1A

```
                                                                    1080
ACTAATCATTCAAAACCCAAATTCAAATATCTAACATTAGTTATTGACCGCCAATAGATG
                                                                    1140
AGAGTTGGTGAGACAGGCTATAAAAGCCCGGCACCCACAACCAGCTTTCTCAAGCCAACT
                                                                    1200
CCAAGCACTTGAGTTCTCTTTTCTTCCTCAACTTAATCTTAAGCTTCAATTTCATTACGT

ATCTAGCATCCATGG
```

FIGURE 1B

Figure 1. Schematic representation of the binary DNA vector pCGN8132 for plant transformation.

องก6,072,103

SEQUENCE LISTING

```
<160> NUMBER OF SEQ ID NOS: 6

<210> SEQ ID NO 1
<211> LENGTH: 1218
<212> TYPE: DNA
<213> ORGANISM: Vitis vinifera
<220> FEATURE:
<221> NAME/KEY: misc_feature
<222> LOCATION: (678)..(810)
<223> OTHER INFORMATION: ozone responsive sequence
<220> FEATURE:
<221> NAME/KEY: misc_feature
<222> LOCATION: (810)..(941)
<223> OTHER INFORMATION: pathogen responsive sequence

<400> SEQUENCE: 1
actatagggc acgcgtggtc gacggccctg gcaaatatat tggcaagtga tgcaggcgac      60
aggtaaatat ttttttttaca gacttctctt tcaataattc tgttgtttat taaaacaaat    120
gtggcattta tattaaactg ctttaatata tttaagaatg ttataaagta ttgttaaaat    180
gctcttatag tcaacatcca ctgtcgtggg tcctatgata tgcacatatg ataaatatac    240
acgtataatg ctattatatg atgcacacgt tattacacga tatttaattt gtgactttct    300
tatgggtaca aattaaaatt tgtaccaatt tttgacttgg caaccaaagt cattgatatt    360
ttccaagtta aaatttgtac caattaaaat ttgtacaatt ttccaatgag tttgcaaaat    420
tctaatgcta tgaagatatt ttcaaatcaa atttatgtga acaaaaatta aagtagtagt    480
tattttccaa gttatttcgt ggatatttga tggagacttg tatttttgat ctacttattt    540
atttatttat ttttaagaat caaacgaatg cgccccagcg tcttgtatcg cggaataggt    600
cagatacaaa tgagatattt gttcaattac tatgtgaata ggttaaatga catgtgacgt    660
tatcctggag aagaaagata gtgggttgtt gagattatta cttctaattg agaaatccat    720 cttttgaatga ccttgtcatg aggaatgatg gtagcagctt cccagccgtg gaaaagtcaa    780
atgaacaaag tattaatttc cagtaagagg ttggagaagt ctttgtctct ctatataaaa    840
```

```
aatgtttctc tttagccgtg accggattga atgctcgctc ctttctgtgg atgcacgcat      900
cgtatatggg taggtgaaga acagataaga atgaagagac aacacgcgcg aatacataaa      960
cacctacaca tacatgtctg aaaatccaaa ataaactcaa gcacacaagc tttgaagcca     1020
actaatcatt caaaacccaa attcaaatat ctaacattag ttattgaccg ccaatagatg     1080
agagttggtg agacaggcta taaaagcccg gcacccacaa ccagctttct caagccaact     1140
ccaagcactt gagttctctt ttcttcctca acttaatctt aagcttcaat ttcattacgt     1200
atctagcatc catgggrb                                                    1218

<210> SEQ ID NO 2
<211> LENGTH: 27
<212> TYPE: DNA
<213> ORGANISM: Synthetic oligonucleotide

<400> SEQUENCE: 2
taggatccat ggcttcagtt gaggaat                                           27

<210> SEQ ID NO 3
<211> LENGTH: 31
<212> TYPE: DNA
<213> ORGANISM: Synthetic oligonucleotide

<400> SEQUENCE: 3
gcgaattcct atttgataca ttacgccatt g                                      31

<210> SEQ ID NO 4
<211> LENGTH: 19
<212> TYPE: DNA
<213> ORGANISM: Synthetic oligonucleotide

<400> SEQUENCE: 4
actatagggc acgcgtggt                                                    19

<210> SEQ ID NO 5
<211> LENGTH: 40
<212> TYPE: DNA
<213> ORGANISM: Synthetic oligonucleotide

<400> SEQUENCE: 5
tagagctctg cagttcaatg ctgcatccct accaagtcta                             40

<210> SEQ ID NO 6
<211> LENGTH: 22
<212> TYPE: DNA
<213> ORGANISM: Synthetic oligonucleotide

<400> SEQUENCE: 6
gtaatacgac tcactatagg gc                                                22
```

PATHOGEN AND STRESS-RESPONSIVE PROMOTER FOR GENE EXPRESSION

TECHNICAL FIELD

This invention relates to inducible regulation of gene expression to provide a host plant with resistance to pathogen infection as well as abiotic stresses. The invention is exemplified by use of a stilbene synthase promoter from Vitis to give gene expression that is inducible upon pathogen infection.

BACKGROUND

Stilbene synthase (EC 2.3.1.95) is a polyketide synthase catalyzing the synthesis of 3,4'. 5-trihydroxystilbene (resveratrol) from p-coumaroyl-CoA and three molecules of malonyl-CoA. This cytosolic enzyme is confined to a few plant genera. In intact and unchallenged cells, the enzyme is weakly expressed, but it is synthesized de novo upon attack by pathogens. Pathogen-derived elicitors turn on the synthesis of stilbene phytoalexins, which are part of the process of induced resistance in these plants. In grapevine, resveratrol and other hydroxystilbenes with fungicidal potential are the dominating phenols produced under biotic stress.

Several plants including grapevine synthesize resveratrol when attacked by pathogens. Comparative studies have revealed that the model of response against microbial attack depends primarily on the developmental stage of the individual plant cell. In this respect, the systems in parsley, bean, and potato have been established and compared with each other; each individual plant species, is unique with regard to the rate at which gene expression is changed, the duration of the transient stage, and the extent to which the enzymes of the pathway are coordinately produced. Stilbenes with fungicidal potential are formed in several unrelated plant species, such as peanuts (*Arachis hypogaea*), grapevine (*Vitis vinifera*), pine (*Pinus slvestris*) and orchids. A few plants such as spruce and rhubarb contain stilbenes but do not exhibit increased de novo syntheses of stilbenes in response to elicitors.

In grape, stilbenes (resveratrol and its oligomeric derivative viniferin) have antimicrobial activity against *Botrytis cinerea* and *Plasmopara viticola,* the main pathogens of this species. Liswidowati et al, (*Planta* (1991) 18: 307–314) demonstrated that stilbene synthase is rapidly and transiently synthesized in grape cell cultures after elicitation with *B. cinerea*. A clone for grape stilbene synthase has been isolated and it has recently been shown that stilbene synthase, when expressed in transgenic tobacco plants, confers an increased disease resistance against *B. cinerea*.

Temporal expression of stilbene synthesis in grape has been studied by analyzing RNAs present at different stages of elicitation by addition of *Phytophthora camelivora* cell wall to cultures of *Vitis vinifera.* Stationary mRNA levels reached maximal values (approximately 15-fold baseline) 6 hours after the onset of elicitor treatment. It therefore would be of interest to obtain the gene encoding this early onset stilbene synthase and isolate the regulatory elements responsible for the rapid and high level of expression of the coding sequence; the regulatory elements provide a means for controlling gene expression for plant disease and stress resistance.

There is substantial interest in modifying a plant with promoters to afford biotic or abiotic stress-induced transcription and expression of a gene introduced into the plant. Of particular interest are promoters which provide for locally inducible expression of genes. Also of interest is the ability to enhance or modify the properties of other promoters.

RELEVANT LITERATURE

Melchior and Kindl, *Arch. Biochem. Biophys.* (1991) 288: 552–557, reports the induction patterns of pSV25, pSV21 and pSV368 cloned stilbene synthase genes in grape. Hain et al, *Nature* (1993) 361: 153–156, reports the production of transgenic tobacco plants containing stilbene synthase genes from grapevine with increased resistance to *Botrytis cinerea* infection. Sparvoli et al., *Plant Mol. Biol.* (1994) 24: 743–755, reports the cloning and characterization of structural genes required for anthocyanin and stilbene biosynthesis in grape. Wiese et al., *Plant Mol. Biol.* (1994) 26: 667–677, reports the isolation and sequencing of Vst1 , Vst2 and Vst3 stilbene synthase genes from grape (*Vitis vinifera*), and compares the patterns of expression of stilbene synthase genes in elicitor-treated cells.

SUMMARY OF THE INVENTION

Methods and compositions are provided for obtaining plants which have inducible resistance to infection and stress. Nucleic acid constructs are provided which provide for regulated transcription, such as pathogen inducible transcription, in a plant tissue or plant part of interest or in response to external agents such as UV exposure. Particularly, transcriptional regions from grape stilbene synthase genes are joined to DNA sequences of interest and introduced into a plant cell host for integration into the genome to provide for pathogen or stress-induced transcription. Of considerable interest, the expression of the DNA sequences of interest is locally induced at the site of the stress, as opposed to being systemically induced. The constructs provide for modulation of expression of endogenous products as well as production of exogenous products in the plant. Novel nucleic acid constructs also are provided employing a grape stilbene synthase promoter, particularly a promoter from a gene which delivers rapid and high level of expression upon infection or elicitation, joined to a DNA sequence of interest and a transcriptional termination region. A DNA construct is introduced into a plant cell host for integration into the genome and transcription regulated upon infection or elicitation. In this manner, high levels of RNA and, as appropriate, polypeptides are achieved at the time of infection or elicitation.

BRIEF DESCRIPTION OF THE DRAWINGS

FIG. 1(A–B) shows the nucleotide sequence (SEQ ID NO:1) of the promoter region of a grape stilbene synthase genomic clone, STS8. The STS8 promoter clone also contains a partial coding sequence of the stilbene synthase. The partial coding sequence begins at the ATG located at nucleotides 1212–1214.

DESCRIPTION OF THE PREFERRED EMBODIMENTS

Figure 2:
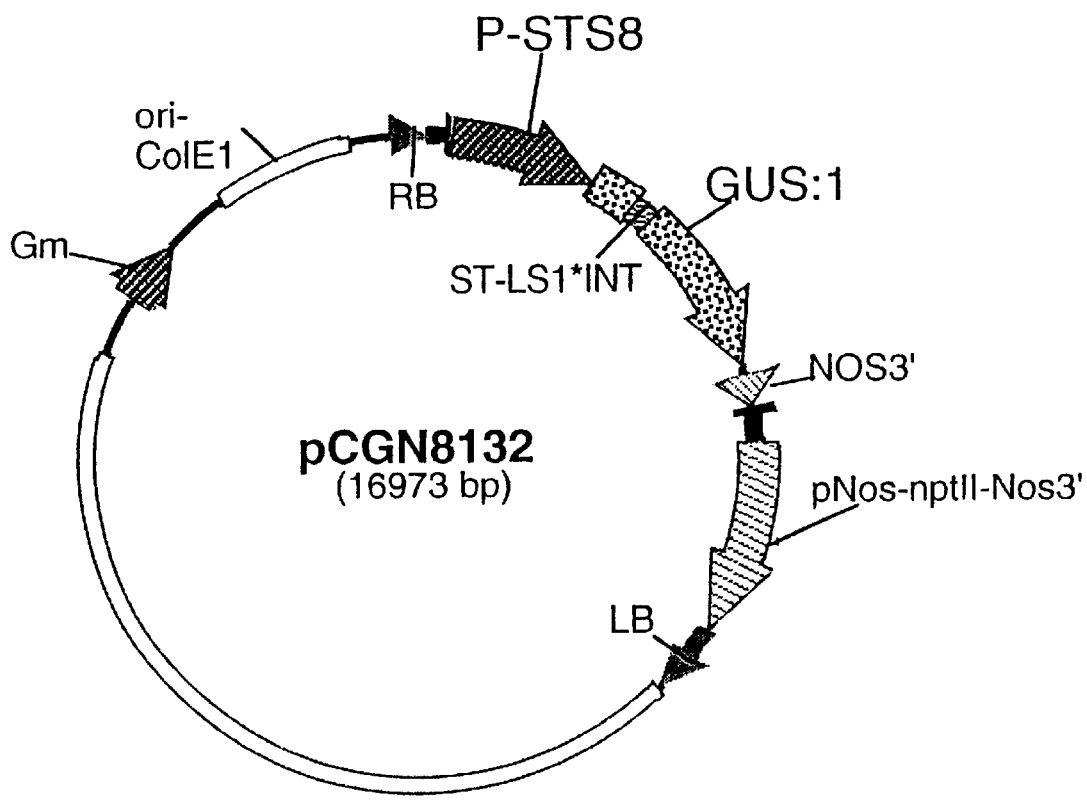
FIG. 2 shows a schematic representation of the primary DNA vector pCGN8132 for plant transformation.

In accordance with the subject invention, nucleic acid constructs are provided which allow for regulated modification of plant phenotype in response to stress, for example, UV exposure, fungal elicitors, interactions with microorganisms, and wounding. The nucleic acid constructs comprise a regulated transcriptional initiation region derived from a locally and rapidly inducible stilbene synthase gene, particularly one having the characteristics of a transcriptional initiation region derived from a SV25 stilbene synthase gene from *Vitis vinifera.* Constructs can be included in a transcriptional cassette or an expression cassette in which downstream from the regulated transcriptional initiation region is a nucleotide sequence of interest which provides for regulated modification of plant phenotype, by modulating the production of an endogenous product, as to amount, relative distribution, or the like, or production of an exogenous expression product to provide for a novel function or product. One or more introns also may be present. Depending upon the manner of introduction of the nucleic acid construct into a host plant, other DNA sequences may be required such as sufficient T-DNA from an *Agrobacterium plasmid* for transfer to a plant host. Plant hosts of particular interest are fruit plants, such as strawberry and tomato.

The rapidity and strength of induction of gene expression provided by the transcriptional activators of the present invention are particularly advantageous where it is desired to trigger or greatly enhance plant resistance responses to pathogen, and pests, or to increase the effectiveness of mechanisms that protect against abiotic stresses (e.g., antioxidant enzymes, wound repair, and repair of genetic damage from UV irradiation). In this manner, the DNA sequences of interest are only expressed at the time of infection and in the area of infection, which specificity may avoid potential deleterious effects to the plant which constitutive expression of such sequences may cause.

The desired effects on plant resistance may be achieved by regulating the production of phytoalexins (e.g., hydroxystilbenes), the expression of disease resistance genes, such as R genes, defense induction genes, such as avr genes, and genes for resistance to insects or nematodes, for example. Examples of genes which may be expressed under the regulatory control of the stilbene synthase promoter constructs of the present invention for enhanced disease resistance are described in Hammond-Kosack, K. E. and Jones, J. G. D. ("Plant disease resistance genes", *Annu. Rev. Plant Pathol.* (1997) 48:575–607) and Bowles, R. J. ("Defense-related proteins in higher plants", *Annu. Rev. Biochem.* (1990) 59:873–907).

The ability to achieve high-level inducible transgene expression is also of considerable importance in "molecular farming", wherein plants are used to produce industrial or pharmaceutical polypeptides and other biopolymers that are foreign to plants. It is also expected that the transcriptional initiators of the present invention will be advantageous for use in reporter gene constructs to develop sensitive and rapid cell-based screens for environmental and agricultural monitoring. As well, it is expected that the present invention can be used to increase the production of pharmaceutically important secondary metabolites in transgenic plants by overexpression of heterologous genes or suppression of endogenous genes in plant metabolic pathways.

The desired transcriptional initiation region is one which is activated at or shortly after pathogen infection or elicitation by abiotic stresses, such as UV irradiation, and wounding. An example of a desired transcriptional initiation region is the one referred to herein as STS8. The STS8 transcriptional initiation region is activated within one hour after infection and remains active until at least 72 hours postinfection. Importantly, transcription from the STS8 promoter is induced locally at the site of elicitation or infection. Local induction is preferred in plant gene expression in cases where it is desired to provide resistance to invading pathogens, particularly fungal or bacterial pathogens.

The identification of transcriptional initiation regions having the desired characteristics can be accomplished in a number of ways. For example, genomic or cDNA libraries can be prepared from a known source of pathogen- and elicitor- inducible stilbene synthase genes such as grapevine, peanut, pine and orchid plants. A library from a given species is screened with oligonucleotide probes designed to contain sequences that are complementary to coding regions of other known inducible stilbene synthase genes. Alternatively, oligonucleotide probes can be designed on the basis of amino acid sequence information obtained from purified stilbene synthase proteins. Oligonucleotide probes based on amino acid sequences can be degenerate or can be biased to favor the preferred codons of the source plant. Oligonucleotides primers can be designed for use in reverse transcription -polymerase chain reaction (RT-PCR) to amplify PCR fragments for cloning and sequencing. The sequences of the PCR fragments can be compared with known coding regions of desired stilbene synthase genes to identify corresponding clones. As an example, the cDNA of a highly inducible, pathogen responsive stilbene synthase gene is obtained by RT-PCR, using the total RNA prepared from pathogen-infected plant tissue and gene-specific primers. The cDNA then is used as bait for isolating the promoter region using genomic restriction libraries from the plant tissue in consecutive PCR reactions with nested primers. The PCR amplification products are cloned and sequenced. The sequence products are then compared with the known coding sequence of the stilbene synthase gene. Additional sequences comprising about 200 bp to about 1500 bp upstream from the start codon are identified and clones that contained upstream sequences are then evaluated for desired promoter activity. The transcriptional initiation region may be native or homologous to the host or foreign or heterologous to the intended host. The term "foreign" is intended to mean that the transcriptional initiation region is not usually found in the plant host into which it is introduced.

In addition to the use of the entire transcriptional initiation regions of the present invention, the use of regulatory elements within the promoters to enhance or modify the properties of other plant promoters is also considered herein. For example, use of an approximately 130 bp region from nucleotides −456 to −324 of the STS8 promoter (nucleotides 678–810 of FIG. 1) may provide an ozone response induction. In addition, an approximately 130 bp fragment located at nucleotides −324 to −193 of the STS8 promoter (nucleotides 810–941 of FIG. 1) may be used to add pathogen induction features to other plant promoters.

A nucleotide sequence of interest is inserted downstream from and under the regulation of the transcriptional initiation region. The nucleotide sequence of interest provides for modification of plant phenotype for example by altering the production of an endogenous product, as to amount, relative distribution, or the like, or by encoding a structurally or functionally novel gene product. The nucleotide sequence may have any open reading frame encoding a peptide of interest, for example, an enzyme, or a sequence complementary to a genomic sequence, where the genomic sequence may be an open reading frame, an intron, a non-coding leader sequence, or any other sequence where the complementary sequence inhibits transcription, messenger RNA processing, e.g., splicing, or translation. The nucleotide sequence of interest may be synthetic, of natural origin, or combinations thereof. Depending upon the nature of the nucleotide sequence of interest, it may be desirable to synthesize the sequence with plant preferred codons. The plant preferred codons may be determined from the codons of highest frequency in the proteins expressed in the largest amount in the particular plant species of interest.

The termination region is one which is functional in a plant host cell. In addition to containing at least one terminating sequence, the termination region can include a poly A signal. In view of the relative interchangeability of the termination regions, the selection of a termination region for use in the expression construct is primarily based on convenience. The termination region and the transcriptional initiation region, or the termination region and nucleotide sequence of interest can originate from the same or different sources. Convenient termination regions are available from the Ti-plasmid of *A. tumefaciens*, such as the octopine synthase gene and nopaline synthase gene termination regions.

Additional DNA sequences can be included in the transcription cassette, for example, adapters or linkers for joining the DNA fragments in the proper orientation and, as appropriate, in the proper reading frame. Other DNA sequences may be needed to transfer transcription constructs into organisms used for transforming plant cells, e.g., *A. tumefaciens*. In this regard, the use of T-DNA of the Ti- or Ri- plasmids as a flanking region in a transcription construct is described in EPO Application No. 116,718 and PCT Application Nos. W084/02913, 02919 and 02920. See also Herrera-Estrella, *Nature* (1983) 303:209–213; Fraley et al., *Proc. Natl. Acad. Sci*, USA (1983) 80:4803–4807; Horsch et al., *Science* (1984) 223:496–498; and DeBlock et al., *EMBO J.* (1984) 3:1681–1689.

The expression constructs of this invention, which contain the regulated 5'-untranslated regions of locally inducible stilbene synthase genes, are transformed into plant cells to evaluate their ability to function with a structural gene other than the open reading frame that is natively associated with the 5'-untranslated region and to ascertain their induction characteristics in response to a particular stimulus, such as infection with *Botyritis*.

In addition, the use of the STS8 transcriptional initiation region of the present invention for expression of stilbene synthase genes for providing increased resistance to plant diseases, particularly fungal or bacterial diseases, is considered in the present invention. Such constructs may express STS genes naturally regulated by the STS8 gene promoter, but preferably in host plants other than grape, or may express other stilbene synthase genes not naturally under transcriptional control of the STS8 promoter. The stilbene synthase genes in such constructs may contain native intron regions associated with the stilbene synthase genes, or may be designed to remove any intronse. Of interest is the use of such constructs to increase plant resistance to diseases, such as those caused by fungi, including Fusarium and Verticillium, and bacterial diseases, such as bacterial root rot.

A variety of techniques are available for the introduction of DNA into a plant cell host. These techniques include transformation employing Ti-plasmid DNA and *A. tumefaciens* or *A. rhizogenes* as the transforming agent, protoplast fusion, injection, electroporation, and the like. The transcription construct normally is joined to a marker that allows for selection of transformed cells in the treated population, for example, resistance to antibiotics such as kanamycin, G418, bleomycin, chloramphenicol and others.

Any plant variety may be employed as a host cell in accordance with this invention. Of particular interest are agricultural fruit crops, such as strawberries and tomatoes, although the use of the STS8 transcriptional initiation region in other plants, including other fruit-bearing plants is also considered. Examples of plants in which the STS8 transcriptional constructs may find use include grain plants, such as wheat, barley, rye, oats and rice; oilseed crop plants such as soybean, oilseed Brassica plants, including canola and high erucic acid varieties, maize, sunflower, safflower, oil palm, and peanut; forest plants, such as firs, spruces, pines and oaks; fruit plants, such as apple, melon, citrus, grape, banana, coconut and pineapple; and other various crop plants including cotton, cocoa, tobacco, and potato.

The transformed plant host cells are used to regenerate plants. See, e.g., McCormick et al., *Plant Cell Reports* (1986) 5: 81–84. These plants are then grown and pollinated with either the same transformed strain or with different strains, and the resulting hybrid having the desired phenotypic characteristic identified. Two or more generations may be grown to ensure that the desired phenotypic characteristic is stable maintained and inherited and then seeds harvested to ensure the desired phenotype or other property has been achieved.

The following examples are offered by way of illustration and not by way of limitation.

EXPERIMENTAL

Materials and Methods

Cloning vectors

The pCR2.1 TA cloning vector was obtained from Invitrogen.

A binary vector for plant transformation, pCGN5928, was constructed using the neomycin phosphotransferase (nptII) kanamycin resistance gene driven by the nopaline synthase transcriptional initiation region (nos 5') and transcription termination (nos 3') sequences( Fraley et al., *Proc. Natl. Acad. Sci* (1983) 30:4803–4807 and Depicker et al., *J. Molec. Appl. Genet.* (1982) 1: 552–573). Both the nos 5' and nos 3' were PCR amplified from the *Agrobacterium tumafaciens* strain C58 and linked together with the nptII gene from pCGN783 (Houck, et al., *Frontiers Appl Microbiol* (1988)4 ) as an EcoR I fragment to form pCGN5908. The nos 5'-nptII-nos3'fragment was then cloned into pCGN1541, containing ori322, Right border (0.5 Kb), lacZ, Left Border (0.58Kb), as an Xho I fragment between the Right border-lacZ and Left border sequences to create the intermediate pCGN5910. The ColEI and pRi origins of replication as well as the Gentamycin resistance gene were aquired from a Not I deleted derivative of pCGN1532 ( McBride and Summerfelt, *Plant Molecular Biology,* (1990), 14:269–276) as a BamH I fragment to create pCGN5924. Finally, a linker containing unique restriction sites was synthesized and cloned into the Asp 718/ Hind III ( within the lacZ sequence) sites of pCGN5924 to create the binary vector pCGN5928.

Materials

Tth DNA polymerase and GenomeWalker® kit (previously known as PromoterFinder kit) were obtained from Clontech.

Sources of additional enzymes and reagents are as folows. Restriction enzymes: Dra I, EcoR V and Sac I were provided with the GenomeWalker kit; Pvu II and Stu I were obtained from Boehringer Mannheim Enzymes: Reverse transcriptase was from Boehringer Mannheim; ligase was provided in GenomeWalker kit.

Chemicals: deoxynucleotides were from Clontech's Advantage® Genomic PCR kit and general chemicals were from Sigma Chemicals.

EXAMPLE 1

Cloning of the STS8 Promoter

1A. Preparation of grape genomic restriction libraries

To isolate grape genomic DNA, fresh tissue was ground to a fine powder in liquid nitrogen using a chilled mortar and pestle. The powder was added to DNA extraction buffer (200 mM CHES (2-(N-Cyclohexylamino)ethanesulfonic acid) /NaOH pH 9.1, 200 niM NaCl, 100 mM EDTA pH 9.0, 2% SDS, 0.5% Sodium deoxycholate, 2% Nonidet NP-40, 20 mM β-mercaptoethanol) and the sample incubated at 65° C., for 10 minutes. Potassium acetate was added to a concentration of 1.1 M, followed by incubation on ice for 30 minutes. The DNA was centrifuged at 20,000× g for 20 min at 4° C. The supernatant was filtered through two layers of Miracloth® ( Calbiochem, La Jolla, Calif.). The DNA was again centrifuged as before. DNA was precipitated by adding 15 mls of isopropanol and centrifuging for 25 minutes at 25,000× g. The pelleted DNA was resuspended in TE (10 mM Tris, 1 mM EDTA). Optical grade Cesium Chloride ( 0.97 g/ml) and 3 mg ethidium bromide were added to the DNA solution. The DNA was then ultracentrifuged at 65,000 rpm for 18 hrs at 15° C. The DNA was extracted with water saturated 1-butanol to clarity. The DNA was then precipitated by adding two volumes of 100% ethanol and centrifuging for 25 minutes at 8,000× g. The DNA pellet was resuspended in 200ul TE.

Grape DNA restriction libraries were constructed from grape genomic DNA as instructed in the GenomeWalker kit. Genomic DNA was digested individually with 5 different blunt end restriction enzymes; Dra I, EcoR V, Pvu II, Sca I and Stu I. After digestion, the GenomeWalker Adapters (48 bases) were ligated to both ends of the restriction fragments to create the restriction libraries.

1B. Isolation of STS cDNA

*Botrytis* infected grape leaves to be used as an RNA source were prepared as follows. A. *Botrytis cinerea* strain Cal 1 spore suspension of $10^6$ was used to spray inoculate detached grape leaves. Inoculated grape leaves were incubated at 20° C., 12 hour light period for 3 days in humidified trays. Leaves were collected at 3 days post inoculation and used for RNA extractions. Grape RNA was extracted using an adaptation of the method described by Loulakakis, K. A., Roubelakis-Angelakis, K. A., and Kanellis, A. K., *American Journal of Enology and Viticulture* (1996) 47: 181–185. The cesium chloride gradient step described in this reference was omitted.

The cDNA of a stilbene synthase gene was obtained by the technique of reverse transcription-polymerase chain reaction (RT-PCR), using the total RNA prepared from *Botrytis* infected grape leaves and the stilbene synthase gene-specific primers:
RES1 5' TAGGATCCATGGCTTCAGTTGAGGAAT 3' (SEQ ID NO:2)
RES2 5' GCGAATTCCTATTTGATACATTACGCCATTG 3' (SEQ ID NO:3) The nucleotide sequences of the primers were designed according to the published sequence of a highly pathogen-inducible STS gene, pSV25 [Melchior and Kindl, *Arch. Biochem. Biophys.* (199L) 288: 552–557]. RES1 is the forward primer containing STS gene encoding sequence from the 5' end of the cDNA, including the ATG start codon (underlined above) and restriction cloning sites. RES2 is the reverse primer containing complementary sequence to bases 1208 to 1232 in the 3' untranslated region (numbering according to Melchior and Kindl) and restriction cloning sites.

Following PCR using RES1 and RES2 primers and RNA prepared as described above , the resulting approximately 1280 base pair STS gene fragment was digested with restriction enzymes EcoR I and BamHI and cloned into pBluescript II SK- (Stratagene) to create pCGN8105. The nucleotide sequence of the cloned STS cDNA (designated STS8) was determined by automated sequencing using M13 Forward and Reverse primers.

No product was obtained when the total RNA from healthy grape leaves was used, suggesting that the cloned STS gene is only expressed during infection.

1C. PCR cloning of the stilbene synthase gene promoter

For the cloning of the STS promoter, the sequence of the cDNA obtained as described in the previous section was used as a template for isolating the promoter region using the GenomeWalker kit from Clontech. The GenomeWalker kit is a PCR-based kit for genome walking in uncloned genomic DNA.

The grape genomic restriction libraries prepared as described above were used in consecutive PCR reactions with nested primers. The primary reaction was performed using a primer specific for the ligated GenomeWalker adapter, AP1, (SEQ ID NO: 1) (5'-GTAATACGACTCACTATAGGGC-3') and STS gene-specific primer, RES2 (described above). In addition to the oligonucleotide primers (0.2μM each), the PCR reaction mix contained 0.2 mM each of DATP, dCTP, dGTP and dTTP, 1.0% glycerol, 0.2 mM Tris-HCl (pH 8.3), 4.6 mM KCl, 1.5 mM EDTA, 15 μM dithiothreitol, 7.3 μgm/ml BSA, 1.1 mM KOAc and 0.1 units Tth DNA polymerase. The mixtures were amplified using the following conditions: 7 cycles of 94° C. for 2 seconds, 72° C. for 3 minutes, 32 cycles of 94° C. for 2 seconds, 67° C. for 3 minutes and 1 cycle of 67° C. for 4 minutes in a Perkin-Elmer 9800 thermocycler. The secondary PCR reaction was performed with primers internal to the primary PCR primers. The GenomeWalker specific primer was AP2: 5'-ACTATAGGGCACGCGTGGT-3' (SEQ ID NO:4) and the stilbene synthase gene-specific primer was RES-I1: 5'-TAGAGCTCTGCAGTTCAATGCTGCATCCCTACCA AGTCTA-3' (SEQ ID NO:5). RES-I1 is the reverse primer containing complementary sequence to nucleotides 309 to 335 of the STS8 stilbene synthase cDNA and restriction cloning sites. The second PCR reaction was run using the same buffer conditions as in the primary reaction and under the amplification conditions of 5 cycles of 94° C. for 2 seconds, 72° C. for 3 minutes, 20 cycles of 94° C. for 2 seconds, 67° C. for 3 minutes and 1 cycle of 67° C. for 4 minutes.

The major products from the PCR reaction were cloned into the pCR2.1 TA vector (Invitrogen) and sequenced. The sequence products showed identity in the coding region to the STS gene, and included an additional 200 to 1200 bp upstream sequence from the start codon, depending on the size of the template fragment from the restriction library. One clone which contained 1211 bp upstream sequence was designated as the promoter STS8. This clone, pCGN8123, also included approximately 700 bp of stilbene synthase encoding sequence, including an intron of 359 bp.

EXAMPLE 2

Sequence analysis of the promoter region

Sequence of the STS8 promoter element was aligned with the stilbene synthase vst1 promoter sequence from grape. Alignment of the STS8 promoter sequence from −460 to the start codon (ATG), including 76 bp of the untranslated leader sequence, shows a 51% identity to the −430 to ATG ( including 73 bp of the untranslated leader) sequence of the vst1 transcript. Two regions, −430 to −280 and −280 to −140, have been identified in the vst1 promoter as being responsible for ozone and pathogen inducibility respectively (Schubert, et al. (1997), Plant Molecular Biology, 34:417–426, and references therein). Alignment of the sequence −430 to −280 upstream from the transcription start of vst1 with the STS8 promoter revealed a 61% identity with the sequence −456 to −324 of the STS8 promoter (nucleotides 678–810 of FIG. 1). The sequence −280 to −140 upstream from the transcriptional start of vst1 has been identified as important for pathogen response. A comparison of this sequence with STS8 showed that the sequence between −324 and −193 of STS8 (nucleotides 810–941 of FIG. 1) is 76% identical to the pathogen responsive sequence of vst1. Alignment of the −193 to −1 region of the STS8 promoter (nucleotides 941–1135 of FIG. 1) with the −40 to −1 region of the vst1 promoter region indicates that the STS8 promoter region contains 2 small insertions (approximately 15 and 30 nucleotides) which are not present in the corresponding region of the vst1 promoter.

EXAMPLE 3

Construction of an Expression Construct

3A. Preparation of a promoter-reporter gene construct

A DNA fusion construct of the promoter with a reporter gene encoding β-glucuronidase (GUS) was made as follows. The STS8 promoter from pCGN8123 was ligated to the 5' end of GUS3 gene-NOS 3' terminator fusion fragment as a Sal 1-Nco 1 fragment, yielding the plasmid pCGN8131. The GUS-NOS fragment was prepared as follows. A 1.8Kb fragment encoding β-glucuronidase (GUS) from *Escherichia coli* (Jefferson et al., *Proc. Natl. Acad. Sci.* (1986) 83:8447–8451) was linked to the nopaline synthase 3' non-translated region nos 3' 0.3Kb) of *Agrobacterium tumefaciens* T-DNA ( Fraley et al., *Proc. Natl. Acad. Sci* (1983) 80:4803–4807 and Depicker et al., *J. Molec. Appl. Genet.* (1982) 1: 562–573) to generate the GUS-NOS terminator fusion. The GUS gene included an intron acquired from the second intron (IV2) of the ST-LS1 gene of potato (Vancanneyt et al., *Mol. Gen. Genet.* (1990) 220:245–250).

3B. Preparation of expression vector

The STS8-GUS-NOS 3' cassette from pCGN8131 was cloned into the binary vector pCGN5928 as a Not 1 fragment, yielding the pCGN8132 expression vector shown in FIG. 1.

3C. pCGN8132 was transformed into *Agrobacterium tumefaciens* strain LBA4404 by the method of Holsters et al., *Molecular and General Genetics* (1979) 163:181–187.

EXAMPLE 4

Evaluation of STS8 promoter function in transformed plants

4A. Transformation of tomato plants

The vector pCGN8132 was introduced into tomato plants by *Agrobacterium*-mediated transformation according to Fillatti et al. (*Bio/Technology,* (1987) 5:726–730). Positive transformants were identified as plants that were resistant to 150μg/ml kanamycin.

Positive transformants were assayed for inducible promoter function by staining Botrytis challenged detached leaf tissue with 5-bromo-4-chloro-3-indole-β-D-glucuronide (X-Gluc) at 24 hour time points. Detatched transformed tomato leaves were inoculated with a single drop, 100 μl, of *Botrytis cinerea* strain Cal 1 spore suspension of $10^6$ conidiospores/ml along the midvein. Inoculated leaves were incubated at 20° C. with 12 hour light period in humidified plastic trays. At 24 hour time points, leaves were collected and infiltrated with GUS buffer (50 mM Potassium Phosphate (pH 7 ), 1 mg/ml X-Gluc and 0.1% Triton X-100), allowed to stain overnight at 37° C. The following day, leaves were destained with washes of 1 hour using 70% ethanol and 4 to 6 hours using 100% ethanol. Inducible expression was characterized by increased GUS staining over the time course which was limited to tissue in area encompassed by a 2 mm circumference surrounding the infection site as well as the infection site itself, which was approximately 5 mm in diameter. This expression pattern provides evidence of a local, as opposed to systemic, pattern of induction.

Twenty kanamycin resistant tomato lines were analyzed for induction of GUS activity. Eight lines showed a weak induction of GUS expression 48 hours post inoculation, five lines showed a mild induction, two lines showed strong induction and five lines showed no induction. Strength of induction was determined by visual inspection of relative color intensity after GUS staining. Weak and mild expression by STS8 showed no GUS staining at 0 hours after inoculation, while the two highest expressing lines had a low basal level of GUS staining at the leaf tips.

In order to determine the speed and duration of induction at the mRNA transcript level, three lines were used for further analysis using Northern hybridizations, two mid level and one high level expresser. Twenty detached leaves from each line were spray inoculated with a spore suspension of *Botrytis cinerea* strain Cal 1 of $10^6$ conidiospores/ml. Inoculated leaves were incubated in a humidified tray at 20° C. Two leaves were collected from each line at time points 0, 1, 2, 4, 8, 12, 24, 48, and 72 hours post inoculation and frozen at −80° C. Total RNA was isolated using TRIzol reagent ( Gibco-BRL Life Technologies) following the manufacturers protocol. Total RNA, 30μg, was separated on a denaturing agarose gel and transferred to nylon membranae (Sambrook et al., 1989). Hybridizations with random primer labeled (using Prime-It II Random Primer labeling kit from Stratagene) GUS 715 fragments were carried out in 35% Formamide, 5× SSC, 0.5× Denhardts, 1% SDS, and 300μg Yeast tRNA, at 42° C.

In the three lines examined, GUS mRNA was expressed within one hour after inoculation, and the signal was sustained for about 48 hours after inoculation. Maximal transcript levels were reached approximately 2 hours after infection.

4B. Transformation of *Nicotinana benthamiana* leaves

Leaves of *Nicotinana benthamiana* were transiently transformed with *Agrobacterium* containing the pSTS8-GUS fusion construct. *Agrobacterium* cells harboring pCGN8132 were grown at 30° C. to the density of 0.8 $OD_{600}$. Cells were washed with sterile water and resuspended in 10 mM $MgSO_4$. Leaves of *Nicotinana benthamiana* were infiltrated with the *Agrobacterium* cell suspension using a sterile syringe without a needle. Infiltrated leaves were allowed to grow for two days before promoter activation as described above for transformed tomato leaves.

Leaves were detached from the plant and placed in a humidified plastic tray. The upper surface of the leaves were inoculated by a drop of 50 μl conidiospore suspension of *Botrytis ciinerea* call at $10^7$ spores/ml.

The activity of the STS8 promoter was determined by examining GUS activity at 24 and 48 hours after infection of Nicotinana leaves with *Botrytis cinerea* using the histochemical staining procedure as described by Stomp, In: GUS Protocols: using the GUS gene as a reporter of gene expression, ed. Gallgdher, S. R., Academic Press, San Diego, USA, 1992, pp. 103–114, and a published fluorometric assay (Jefferson, *Plant Mol. Biol. Reporter* (1987) 5: 387–405).

Histochemical staining was observed at the site of fungal infection indicating that the STS8 promoter was locally inducible by *Botrytis cinerea* infection. Intense staining was observed at the site of infection of Nicotinana leaves. Fluorometric assays showed that GUS activity in infected leaf tissues was significantly increased when compared to healthy uninfected controls.

EXAMPLE 5
STS8 Promoter Driven Expression of Stilbene Synthase cDNA in Tomato A DNA fusion construct of the STS8 promoter with a grape cDNA clone of Stilbene synthase was prepared. A 1.2 Kb STS8 Promoter fragment from pCGN8123 was cloned as a Sal 1-Nco 1 fragment to the 5' end of stilbene synthase with a Nos 3' transcription terminator sequence. The STS8-Stilbene synthase-Nos 3' fragment was cloned into pCGN5928 as a Not 1 fragment to create pCGN8126.

The vector pCGN8126 was transformed into *Agrobacterium tumefaciens* strain LBA4404 by the method of Holsters et al., Molecular and General Genetics (1979) 163:181–187.

The vector pCGN8126 was introduced into tomato plants by *Agrobacterium*-mediated transformation according to Fillatti et al. (*Bio/Technology*, (1987) 5:726–730). Positive transformants were identified as plants that were resistant to 150μg/ml kanamycin.

Forty five tomato lines positive for kanamycin resistance were generated with pCGN8126 and are screened by PCR to confirm the presence of the transgenic stilbene synthase gene. Positive transformants are analyzed for STS8 stilbene synthase gene and accumulation of resveratrol. Selected lines are are selfed to obtain homozygous transformants for use in field trials to test the effects of stilbene synthase gene expression on resistance to plant diseases.

The above results demonstrate that the STS8 promoter can be used to provide for inducible expression of DNA sequences of interest in plants, wherein the response to induction is rapid, the expression is locally induced, and the expression reaches a high level. Such a pattern of expression is particularly desirable for expression of genes related to plant disease resistance, such as the stilbene synthase gene, and may provide for the production of improved plants having enhanced resistance to plant pathogens.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed:

1. A DNA construct comprising:

in the 5'to 3'direction of transcription, a transcriptional initiation region comprising the sequence as set forth in SEQ ID NO: 1, a DNA sequence of interest, and a transcriptional termination regior functional in plants.

2. The DNA construct according to claim 1, wherein said transcriptional initiation region provides for induction of transcription of said DNA sequence of interest within one hour of said pathogen infection or abiotic stress.

3. The DNA construct according to claim 2, wherein said transcriptional initiation region is derived from the STS8 stilbene synthase gene of *Vitis vinifera*.

4. The DNA construct according to claim 1, wherein said DNA sequence of interest is an open reading frare encoding an amino acid sequence.

5. A transcription cassette comprising:

in the 5'-3' direction of transcription, a transcriptional initiation region from a pathogen locally inducible-rapid response grape stilbene synthase gene operably linked to a nucleotide sequence of interest and a transcriptional termination region, wherein said transcriptional initiation region comprises the sequence set forth in SEQ ID NO:1.

6. The transcription cassette according to claim 5, wherein said transcriptional initiation region is derived from the STS8 stilbene synthase gene of *Vitis vinifera*.

7. A DNA construct comprising:

in the 5'–3' direction of transcription, a regulatable transcriptional initiation region from a pathogen locally inducible-rapid response grape stilbene syntliase gene, a linker or polylinker having one or a plurality of restriction sites for insertion of a gene to be expressed under transcriptional control of said transcriptional initiation region, and a transcriptional termination region functional in plants, wherein said transcriptional initiation region comprises the sequence set forth in SEQ ID NO: 1.

8. The DNA construct according to claim 7, wherein said transcriptional initiation region is derived from the STS8 stilbene synthase gene of *Vitis vinifera*.

9. The DNA construct according to claim 7, wherein a DNA sequence of interest heterologous to the stilbene synthase gene is inserted into at least one of said restriction sites.

10. A DNA construct comprising a transcriptional initiation region functional in a plant cell, where said transcriptional initiation region comprises nucleotides 810–941 of the sequence shown in SEQ ID NO:1.

11. A DNA construct comprising a transcriptional initiation region functional in a plant cell, where said transcriptional initiation region comprises nucleotides 941–1135 of the sequence shown in SEQ ID NO: 1.

12. A DNA construct comprising a transcriptional initiation regioti functional in a plant cell, where said transcriptional initiation region comprises nucleotides 941–1135 of the sequence shown in SEQ ID NO:1.

13. A plant or portion thereof each comprising a heterologous DNA construct according to any one of claims 1, 3, 7, 10, 11, or 12.

14. A method for modulating disease resistance in a plant, wherein said method comprises growing a plant which contains in its genome a transgenic construct which provides for expression of a gene under the regulatory control of the STS8 stilbene synthase promoter from grape and wherein said gene is useful for providing resistance to a plant pathogen.

15. The method of claim 14, wherein said gene is, stilbene synthase.

16. An isolated DNA sequence having the sequence of SEQ ID NO: 1.

17. An isolated nucleic acid sequence complementary to the sequence of SEQ ID NO: 1.

18. The DNA construct according to claim 1, wherein said initiation region is derived from a grape stilbene synthase gene.

19. The DNA construct according to claim 1, wherein said initiation region promotes rapid and locally induced initiation of gene transcription in response to pathogen infection and abiotic stresses.

20. The method according to claim 14, wherein said promoter comprises the sequence set forth in SEQ ID NO: 1.

* * * * *